(12) United States Patent
Gregory et al.

(10) Patent No.: US 10,758,151 B2
(45) Date of Patent: Sep. 1, 2020

(54) TECHNIQUES FOR DETECTING CANCEROUS CELLS IN EXCISED TISSUE SAMPLES USING IMPEDANCE DETECTION

(71) Applicant: NovaScan, Inc., Milwaukee, WI (US)

(72) Inventors: William David Gregory, Shorewood, WI (US); John Shell, Milwaukee, WI (US); Paul Richard Voith, Cedarburg, WI (US); Moshe Morrie Altmejd, Austin, TX (US)

(73) Assignee: NovaScan, Inc., Milwaukee, WI (US)

( * ) Notice: Subject to any disclaimer, the term of this patent is extended or adjusted under 35 U.S.C. 154(b) by 135 days.

(21) Appl. No.: 15/870,804

(22) Filed: Jan. 12, 2018

(65) Prior Publication Data

US 2018/0206755 A1  Jul. 26, 2018

Related U.S. Application Data

(60) Provisional application No. 62/499,222, filed on Jan. 23, 2017, provisional application No. 62/603,081, filed on May 16, 2017.

(51) Int. Cl.
| | | |
|---|---|---|
| *A61B 5/053* | (2006.01) | |
| *A61B 5/00* | (2006.01) | |
| *G01N 1/28* | (2006.01) | |
| *G01N 33/487* | (2006.01) | |

(52) U.S. Cl.
CPC ............... *A61B 5/053* (2013.01); *A61B 5/72* (2013.01); *G01N 1/286* (2013.01); *G01N 33/48707* (2013.01); *G01N 2001/2866* (2013.01)

(58) Field of Classification Search
CPC .......... A61B 5/503; A61B 5/0536; A61B 2018/0016; G01N 27/026; G01N 27/04; G01N 33/4836; G01N 33/4833
See application file for complete search history.

(56) References Cited

U.S. PATENT DOCUMENTS

| | | | | |
|---|---|---|---|---|
| 2003/0149363 | A1* | 8/2003 | Dreschel | B06B 1/00 600/437 |
| 2008/0009764 | A1 | 1/2008 | Davies | |
| 2009/0253193 | A1* | 10/2009 | Gregory | G01N 33/4836 435/287.1 |
| 2014/0247082 | A1* | 9/2014 | Gazit | H03K 19/018521 327/333 |

OTHER PUBLICATIONS

"Safeguarding low-level signals." Evaluation Engineering (2015). (Year: 2015).*
International Search Report for application No. PCT/US2018/014662 dated May 10, 2018.
Gregory et al., "The Cole Relaxation Frequency as a Parameter to Identify Cancer in Breast Tissue", Medical Physics, Jul. 2012, vol. 39, No. 7, pp. 1469-1471.

* cited by examiner

*Primary Examiner* — Christopher Adam Hixson
(74) *Attorney, Agent, or Firm* — Artegis Law Group, LLP (57) ABSTRACT

One embodiment of the present application sets forth a method for detecting cancerous cells in a sample of excised tissue. The method includes a first subset of electrodes included in an electrode array measuring, at a first operating frequency, a first impedance of a first section of the sample. The method also includes computing a first Cole relaxation frequency for the first section of the sample based on the first impedance. The method also includes determining that the first section of the sample contains cancerous cells based on the first Cole relaxation frequency.

18 Claims, 7 Drawing Sheets

TECHNIQUES FOR DETECTING CANCEROUS CELLS IN EXCISED TISSUE SAMPLES USING IMPEDANCE DETECTION

CROSS-REFERENCE TO RELATED APPLICATIONS

This application claims priority benefit of the U.S. Provisional Patent Application titled, "RAPID METHOD AND DEVICE FOR DETECTING NON-MELANOMA SKIN CANCER IN MONS MICROGRAPHIC SURGERY (MMS); MARGINSCAN," filed on Jan. 23, 2017 and having Ser. No. 62/499,222. This application also claims priority benefit of the U.S. Provisional Patent Application titled, "COLE RELAXATION FREQUENCY TO DETECT CANCER AND MEASURE THE TISSUE PROGRESS FROM NORMAL (BENIGN) TO CANCER," filed on May 16, 2017 and having Ser. No. 62/603,081. The subject matter of these related applications is hereby incorporated herein by reference.

BACKGROUND OF THE INVENTION

Field of the Invention

Embodiments of the present invention relate generally to medical diagnostic technology, and, more specifically, to techniques for detecting cancerous cells in excised tissue samples using impedance detection.

Description of the Related Art

Mohs micrographic surgery (MMS) is a treatment for skin cancer that is used when removing basal cell carcinomas (BCCs) and squamous cell carcinomas (SCCs). During MMS, a surgeon removes a layer of skin from a target area of a patient that is suspected to include some cancer cells. Immediately after removing the excised layer, frozen sections are prepared the surgeon examines slides under a microscope to determine the presence of cancer cells. According to the procedure, the surgeon successively removes and examines skin layers from the patient until the frozen sections are satisfactorily cleared of diseased tissue. MMS advantageously enables a surgeon to remove a minimal amount of tissue from the patient and preserve a maximal amount of healthy cells around the target excision.

One of the drawbacks of MMS is that excising, examining, and assessing the different layers of tissue suspected to contain cancer cells is quite time-consuming for surgeons. In particular, as alluded to above, for each excised layer of tissue, the surgeon must manually prepare frozen sections and then examine frozen sections under a microscope and assess whether the sample contains any cancer cells. Due to the time-consuming nature of MMS, this particular procedure is considered to be an expensive form of cancer treatment.

As the foregoing illustrates, what is needed in the art are more effective techniques for analyzing and assessing excised tissue layers during Mohs micrographic surgery.

SUMMARY OF THE INVENTION

One embodiment of the present application sets forth a method for detecting cancerous cells in a sample of excised tissue. The method includes a first subset of electrodes included in an electrode array measuring, at a first operating frequency, a first impedance of a first section of the sample. The method also includes computing a first Cole relaxation frequency for the first section of the sample based on the first impedance. The method also includes determining that the first section of the sample contains cancerous cells based on the first Cole relaxation frequency.

A major advantage of the disclosed tissue measurement system is that the system quickly and accurately detects the presence and location of cancer cells within a tissue excised from a patient, without involving the surgeon. Because the disclosed system is able to automatically analyze and assess successively excised tissue layers in an MMS procedure before the preparation of frozen sections, the time required to perform MMS is substantially reduced, thereby making MMS a more cost-effective form of cancer treatment.

BRIEF DESCRIPTION OF THE DRAWINGS

So that the manner in which the above recited features of the invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

In the following description, numerous specific details are set forth to provide a more thorough understanding of the present invention. However, it will be apparent to one of skilled in the art that the present invention may be practiced without one or more of these specific details.

As discussed above, conventional techniques for Mohs micrographic surgery (MMS) require a surgeon to excise and manually prepare frozen sections for microscopic evaluation of excised tissue to determine whether the excised tissue contains any cancer cells. Such a technique is time-consuming and expensive, as the lengthy process requires the surgeon or third party to perform assessments for several frozen sections of each of the excised layers during the surgery.

To address this problem, embodiments of the invention include a tissue measurement system that sends electrical currents to sections of an excised tissue sample. A diagnosis module connected to an electrode array receives electrical measurements and computes electrical properties, including impedances and Cole relaxation frequencies, based on the electrical measurements. The diagnosis module compares a computed Cole relaxation frequency to a cancer-detection threshold to determine whether cancerous cells are present in the corresponding section of the excised tissue sample. In some embodiments, the diagnosis module may determine the locations of the detected cancerous cells within the excised tissue sample.

Though the description discusses tissue samples excised during Mohs micrographic surgery, the disclosed techniques can be executed for other types of excised tissues cells. Further, the disclosed techniques can be executed independently from MMS procedures.

Figure 1:
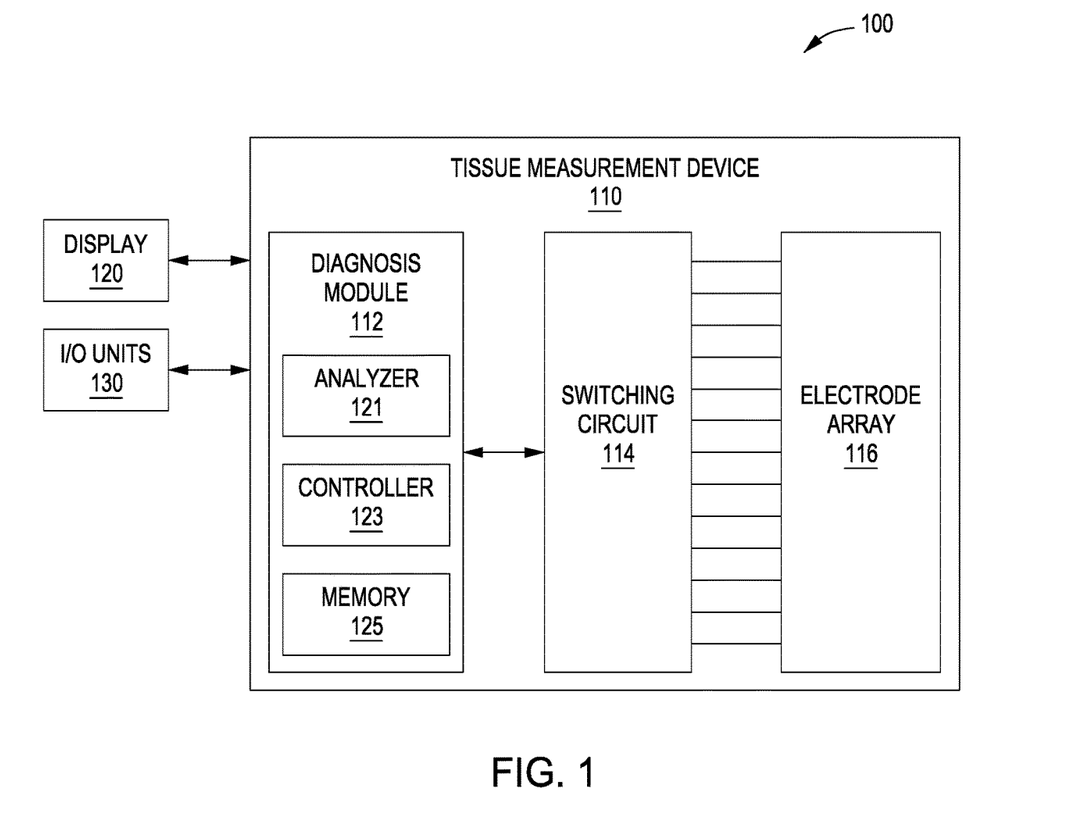
FIG. 1 illustrates a tissue measuring system configured to implement one or more aspects of the present invention.

FIG. 1 illustrates a tissue measuring system configured to implement one or more aspects of the present invention. Tissue measurement system 100 includes a tissue measurement device 110, a display 120, and input/output (I/O) units 130. Tissue measurement device 110 includes a diagnosis module 112, a switching circuit 114, and an electrode array 116. Diagnosis module 112 includes an analyzer 121, a controller 123, and memory 125.

Tissue measurement device 110 automatically measures impedances of a section of an excised tissue sample. Diagnosis module 112 causes switching circuit 114 to select different measuring subsets of electrode array 116 that measure the electrical properties of different sections of an excised tissue sample. In some embodiments, when performing measurements on the section of the excised tissue sample, diagnosis module 112 may perform a sweep of measurements within a range of operating frequencies. For example, a measuring subset of electrode array 116 may initially inject a current at an initial operating frequency between 1 kHz and 25 MHz, then measure and record the electrical properties of the section of the excised tissue sample. Tissue measurement device 110 may then sweep through range of operating frequencies. For example, tissue measurement device 110 may increase the operating frequency of the injecting current at steps of 1 kHz.

Tissue measurement device 110 computes impedances for the electrical properties and subsequently computes a Cole relaxation frequency ($F_{cole}$) from the computed impedances. The Cole relaxation frequency for a section of the excised tissue sample reflects the rate at which a cell membrane discharges a stored electrical charge. In some embodiments, tissue measurement device 110 computes the Cole relaxation frequency as an average of electrical discharge rates for a plurality of cells included in the section of the excised tissue sample. In some embodiments, tissue measurement device 110 may determine the presence and/or location of cancerous cells based on computing Cole relaxation frequencies for one or more sections of the excised tissue sample. In some embodiments, tissue measurement device 110 may output measurement data to display 120 and/or I/O units 130.

In some embodiments, tissue measurement device 110 may include diagnosis module 112, switching circuit 114, and electrode array 116 as separate physical components. In alternative embodiments, diagnosis module 112, switching circuit 114, and/or electrode array 116 may share a common housing. In some embodiments, tissue measurement device 110 may communicate wirelessly with display 120 and/or I/O units 130.

Electrode array 116 includes multiple electrodes that are electrically isolated from each other by intervening channels. In some embodiments, electrode array 116 is planar, allowing an excised tissue sample to be placed directly on one or more electrodes of electrode array 116. In some embodiments, one or more of the electrodes included in electrode array 116 are non-invasive and may have a surface configured to reduce electrical polarization between the individual electrodes of electrode array 116 and the excised tissue sample. For example, one or more of the electrodes in electrode array 116 may have a blackened platinum (BPt) surface that physically contacts a portion of the excised tissue sample, reducing the electrical polarization between the electrode array 116 and the excised tissue sample.

Switching circuit 114 connects electrical signals between electrode array 116 and diagnosis module 112. In some embodiments, switching circuit 114 also includes components of measurement circuits, including a voltmeter and an ammeter. In such instances, switching circuit 114 connects a measuring subset of electrodes from electrode array 116 to the voltmeter and ammeter, respectively, to measure the voltage and current of the section of the excised tissue sample. As will be discussed in further detail below, switching circuit 114 includes an array of individual switches, such as micro-relay circuits, that each connect to a separate electrode in electrode array 116. In some embodiments, the individual switches are controlled by controller 123 in diagnosis module 112 to connect the corresponding electrode to either a current-sensing circuit or a voltage-sensing circuit. Each of the current-sensing circuit and the voltage-sensing circuit may be components of a single measurement circuit. In some embodiments, switching circuit 114 may keep one or more micro-relays included in the micro-relay circuits open, where the connected electrode remains floating and provides a high impedance when a current is injected.

Diagnosis module 112 connects through switching circuit 114 to electrode array 116. In some embodiments, diagnosis module 112 may use controller 123 to execute a program stored in memory 125 to conduct multiple electrical measurements on the excised tissue sample using multiple measuring subsets of electrode array 116. In some embodiments, diagnosis module 112 may receive instructions from a user via I/O units 130 to store data or to perform specific electrical measurements via electrode array 116. In some embodiments, diagnosis module 112 may store the measured electrical properties determined by the measurement circuit, such as the measured voltage and the measured current for an input signal at a specific operating frequency. In some embodiments, diagnosis module 112 can include a processing unit. The processing unit may be a single central processing unit (CPU), or combination of processing units. The processing unit may be any technically-feasible hardware unit capable of processing data and/or executing software code. In some embodiments, the processing unit of diagnosis module 112 may receive instructions from a user or from memory 125 and may execute instructions. In some embodiments, the processing unit may implement one or more techniques executed by analyzer 121 and/or controller 123.

Analyzer 121 of diagnosis module 112 computes real and imaginary impedances for a section of the excised tissue sample based on the measured electrical properties. In some embodiments, diagnosis module 112 stores the computed impedances in memory 125. Analyzer 121 computes the Cole relaxation frequency for the section of the excised tissue sample based on the computed impedances corresponding to the operating frequency. The Cole relaxation frequency for a section of the excised tissue sample reflects the rate at which a cell membrane discharges a stored electrical charge. In some embodiments, analyzer 121 determines whether the section of the excised tissue sample includes cancerous cells. Due to the contrasting electrical properties of malignant cells and non-malignant cells, malignant cells have a Cole relaxation frequency that is over one thousand times smaller than the Cole relaxation frequency of a non-malignant cell. Analyzer 121 compares the compute Cole relaxation frequency to a pre-determined cancer-detection threshold to determine whether the section of the excised tissue sample contains cancerous cells.

In some embodiments, analyzer 121 may determine a probability of malignant cancer cells based on one or more frequency ranges above the cancer-detection threshold. In such instances, each frequency range may indicate that the cancerous cells are more dangerous and may indicate a need for more aggressive treatment. For example, an initial cancer-detection threshold for breast cancer cells may be 100 kHz. A Cole relaxation frequency occurring within a first critical range of 100 kHz to 600 kHz may indicate that the breast cancer may recur after treatment. A Cole relaxation frequency occurring within a second critical range above 600 kHz may indicate a high likelihood of metastasis after treatment. The cancer-detection threshold and the number and thresholds for each of the critical ranges may vary for each type of cancer.

In some embodiments, analyzer 121 may generate an impedance spectrum for a set of computed impedances, which indicates the magnitude of impedances as a function of the operating frequency used during measurement. In such instances, analyzer 121 can compute the Cole relaxation frequency for the set of impedances by performing a regression analysis to find a best fit to pre-determined impedance spectrums stored in memory 125. Analyzer 121 may determine the Cole relaxation frequency from the impedance spectrum by determining the frequency corresponding to the peak impedance of the impedance spectrum.

Controller 123 of diagnosis module 112 causes switching circuit 114 to select different measuring subsets of electrode array 116 that measure electrical properties of different sections of an excised tissue sample. Controller 123 also sets the operating frequency and amplitude of the injection current when initiating a measurement using the measuring subset of electrode array 116. In some embodiments, controller 123 may load instructions stored in memory 125 and execute a measurement program using one or more measuring subsets of electrode array 116. In some embodiments, controller 123 may generate and transmit one or more control signals to switching circuit 114 to open and/or close switches corresponding to different measuring subsets of electrode array 116. Controller 123 may change to a different measuring subset by transmitting a control signal to switching circuit 114 that electrically connects electrodes of the measuring subset to the measuring circuit, while disconnecting all remaining electrodes in electrode array 116.

Memory 125 is configured to store data and/or software applications. Memory 125 may include a random access memory (RAM) module, hard disk, flash memory unit, or any other type of memory unit or combination thereof. Diagnosis module 112 and I/O units 130 are configured to read data from memory 125. Diagnosis module 112 and I/O units 130 are also configured to write data to memory 125.

Display 120 displays data transmitted from tissue measurement device 110. In an embodiment, display 120 displays one or more of the computed Cole relaxation frequency, the location(s) of cancerous cell regions, and the probability of cancer in the excised tissue sample. In some embodiments, display 120 may refresh the data received from tissue measurement device 110 while tissue measurement device 110 performs measurements on the excised tissue sample. In some embodiments, display 120 may display an image of the excised tissue sample with indications of the locations of probable cancerous cells.

I/O units 130 receive output signals from tissue measurement device 110 and transmit input signals from a user to tissue measurement device 110. In some embodiments, I/O units 130 transmit program input signals to controller diagnosis module 112, where diagnosis module 112 stores the program in memory 125. In some embodiments, I/O units 130 may include devices capable of receiving one or more inputs, including a keyboard, mouse, input tablet, camera, and/or three-dimensional (3D) scanner. In some embodiments, I/O units 130 may also include devices capable of providing one or more outputs, such as a speaker or printer. I/O units 130 may also include devices capable of both receiving inputs and providing outputs, such as a touch-screen and a universal serial bus (USB) port.

Figure 2:
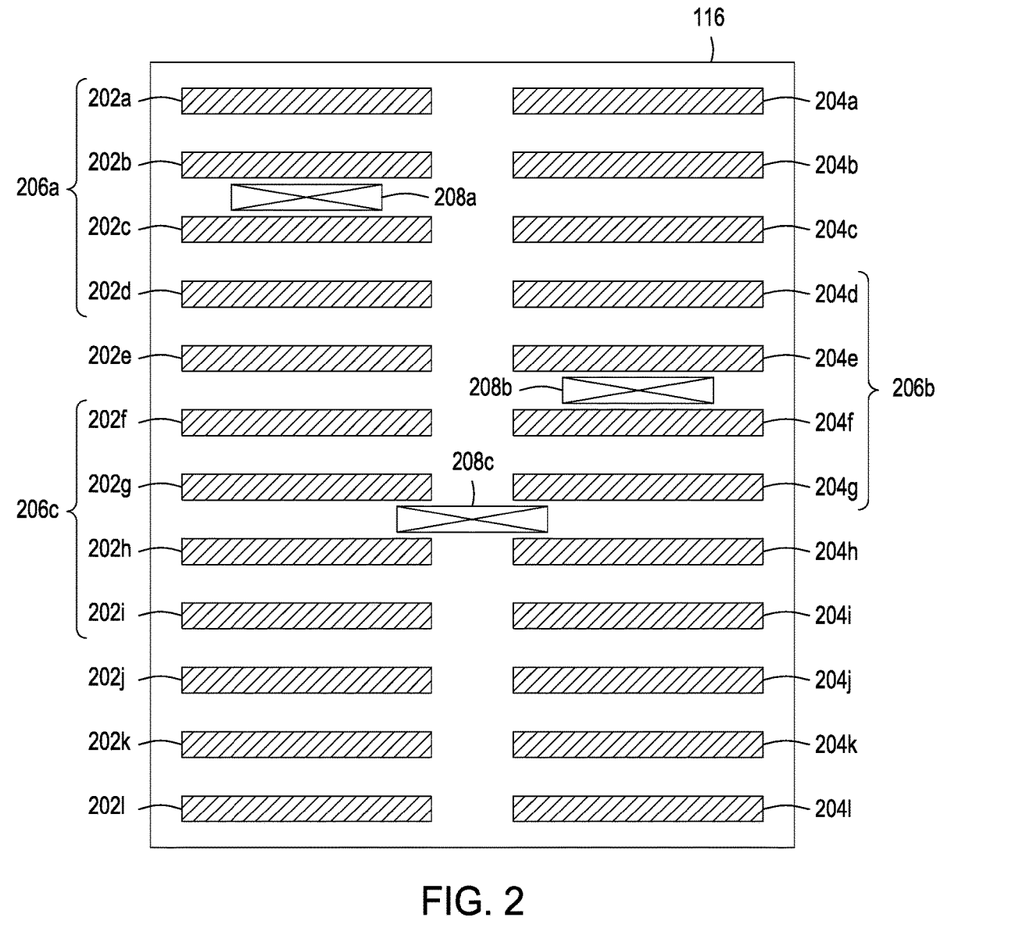
FIG. 2 is a more detailed illustration of the electrode array of FIG. 1, according to various embodiments of the present invention.

FIG. 2 is a more detailed illustration of the electrode array of FIG. 1, according to various embodiments of the present invention. Electrode array 116 includes a first column of electrodes 202a-l and a second column of electrodes 204a-l. In some embodiments, the physical distance between each of the electrodes in electrode columns 202a-l, 204a-l is constant. In some embodiments, the electrical paths of different electrode pairs are constant. For example, the physical distance between electrode 202a and electrode 202b may have a physical distance of 1 mm, which may be equal to a 1-mm physical distance between electrode 204j and 204k. Similarly, an electrical path formed by connecting electrodes 202a, 202b to switching circuit 114 is equal to an electrical path formed by connecting electrodes 204j, 204k to switching circuit 114. In some embodiments, controller 124 through switching circuit 114 selects a measuring subset of electrodes 206a-c where the measuring circuit includes electrodes that have the same path length. Selection of such measuring subset provides the advantage of avoiding synchronization issues by avoiding reflections and phase shifts when performing multiple measurements. In some embodiments, the physical path length and/or the electrical path length of electrodes 202a-l, 204a-l may not be equal, but may be fixed in time. In such instances, subsequent signal processing steps may be adjusted to compensate for unequal physical path lengths and/or unequal electrical path lengths.

During operation, controller 123 may measure the electrical properties of a section of an excised tissue sample located at section 208a by selecting measuring subset 206a of electrode array 116, which includes electrodes 202a-d. Similarly, controller 123 may measure section 208b by selecting measuring subset 206b, which includes electrodes 204d-g. Controller 123 may measure section 208c by selecting measuring subset 206a, which includes electrodes 202f-i, 204f-i. In some embodiments, controller 123 may measure varying depths of the excised tissue sample by selecting a measuring subset with electrodes located further away from the section. For example, when measuring section 208c, controller 123 may measure a different depth of section 208c by selecting a measuring subset including each of electrodes 202c-l, 204c-l. When switching circuit 114 connects measuring subset 206a to the measuring circuit, one or more of electrodes 202a-d may be connected to a voltage-sensing device, one or more of electrodes 202a-d may be connected to a current-sensing device, while the remainder of electrodes 202e-l, 204a-l are disconnected from the measuring circuit.

In some embodiments, an electrode pair of 202a, 202d in measuring subset 206a forms a current-sensing circuit. In such instances, electrode 202a acts as an injection electrode that receives a current from a current generator. The injection electrode 202a receives an alternating current that has a frequency corresponding to the operating frequency specified by controller 123. Electrode 202d acts as a return electrode that completes a current path by connecting to electrode 202a. In some embodiments, the return electrode 202d is connected to a current-sensing circuit or current-sensing device, such as an ammeter. Diagnosis module 112 may receive the current measurement provided by the current-sensing circuit or current-sensing device and associate the measured current with the operating frequency of the initial current.

In some embodiments, one or more electrodes in between the electrodes forming the current-sensing circuit may be part of a voltage-sensing circuit. For example, electrodes 202b, 202c of measuring subset 206a may act as voltage-sensing electrodes and be connected to a voltage-sensing circuit or a voltage-sensing device, such as a voltmeter. Voltage-sensing electrodes 202b, 202c may have a high impedance in order to avoid adding stray currents into the measuring circuit. Diagnosis module 112 may receive the voltage measurement provided by the voltage-sensing circuit or voltage-sensing device and associate the measured current with the operating frequency of the initial current.

Controller 123 may measure different sections of an excised tissue sample by switching to different measuring subsets 206a, 206b, 206c. For example, controller 123 may cause switching circuit 114 to switch from measuring section 208a to section 208b by disconnecting measuring subset 206a from the measuring circuit and connecting measuring subset 206b to the measuring circuit. In some embodiments, controller 123 may switch between sections 208a, 208b, 208c in a pre-defined pattern. For example, controller 123 may perform series of electrical measurements on section 208a for 10 to 60 seconds. Controller 123 may then cause switching circuit 114 to select a different measuring subset to perform a series of electrical measurements on a section of the excised tissue sample located between electrode 202c and 202d for 10 to 60 seconds. In some embodiments, controller 123 may perform electrical measurements all sections within electrode array 116 in under 60 to 120 seconds.

Figure 3:
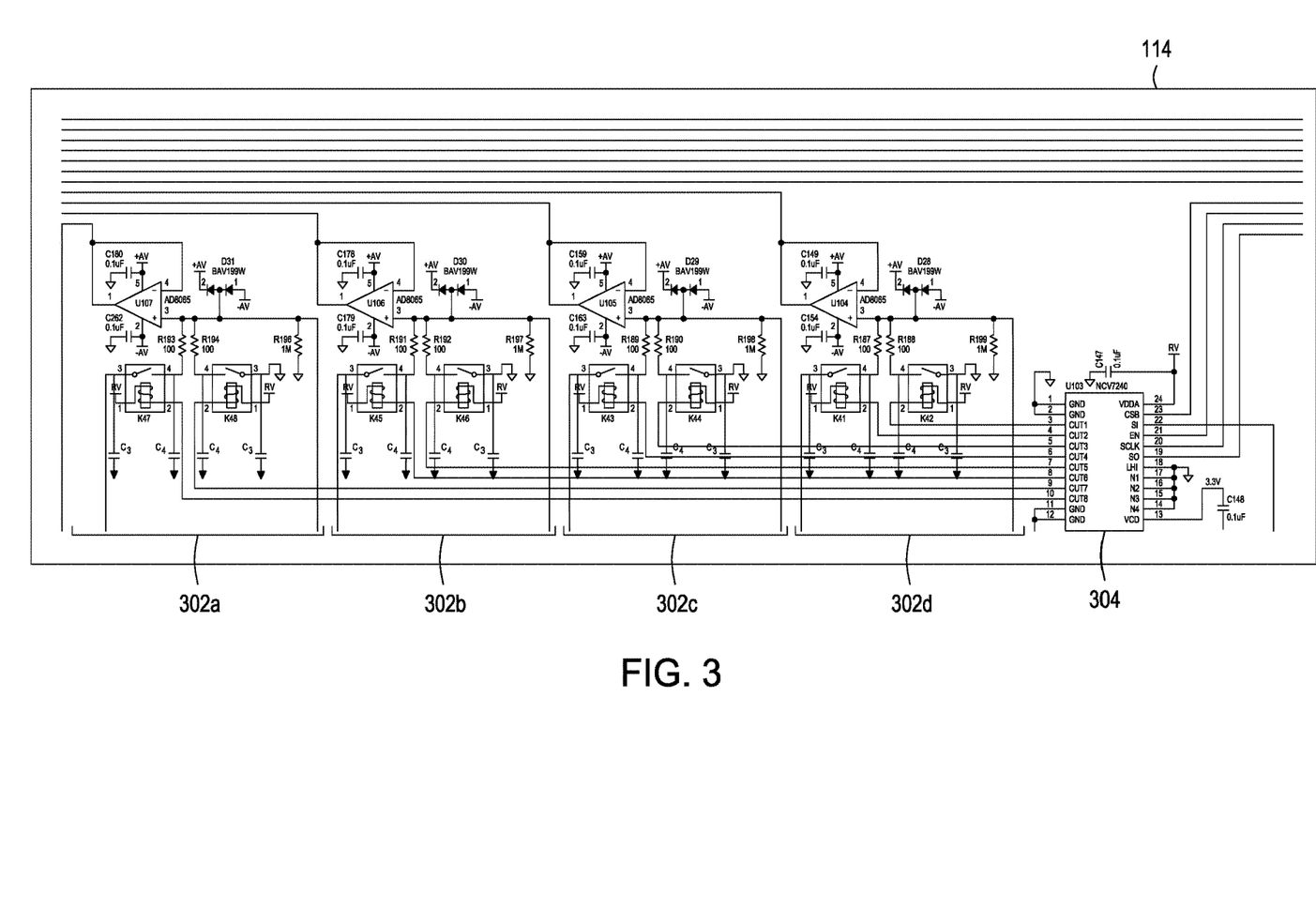
FIG. 3 is a more detailed illustration of the switching circuit of FIG. 1, according to various embodiments of the present invention.

FIG. 3 is a more detailed illustration of the switching circuit of FIG. 1, according to various embodiments of the present invention. Switching circuit 114 includes micro-relay circuits 302a-d connected to relay driver 304. In some embodiments, relay driver 304 may receive one or more control signals from controller 123 and connect one or more electrodes to the voltage-sensing circuit of the measuring circuit and connect one or more electrodes to the current-sensing circuit of the measuring circuit.

Relay driver 304 may be a microcontroller or other electronic circuit that controls one or more micro-relay circuits 302a-d. In some embodiments, one or more relay drivers 304 may control each of the micro-relay circuits connected to the corresponding electrodes in electrode array 116. In some embodiments, relay driver 304 may receive control signals from controller 123 to connect electrodes to the measuring circuit. Relay driver 304 may respond to the received control signal by sending one or more driving signals to micro-relay components included in each of micro-relay circuits 302a-d. The driving signal may close one of the pair of micro-relay components or open each of the micro-relay components. In some embodiments, relay driver 304 switches the measuring subset of electrodes 206a to a separate measuring subset of electrodes 206b by sending driving signals to each of micro-relay circuits 302a-d corresponding to the electrodes included in measuring subsets 206a, 206b.

Each of micro-relay circuits 302a-d is connected to a separate electrode in electrode array 116. In some embodiments, micro-relay circuit 302a-d includes an amplifier and two separate micro-relay components at the input of the amplifier. In some embodiments, relay driver 304 may open both micro-relay components, configuring the circuit to perform voltage sensing at the corresponding electrode in electrode array 116. Relay driver 304 may close the first of the two micro-relay components to connect micro-relay circuit 302a-d and the corresponding electrode to the current injection source. In some embodiments, relay driver 304 may close the second of the two micro-relay components to connect micro-relay circuit 302a-d and the corresponding electrode to the current-sensing circuit. In some embodiments, one or more of the remaining electrodes not in measuring subset 206a may be shorted to ground.

In some embodiments, a two electrode configuration may sense both the current and the voltage. In the two electrode configuration, one electrode in electrode array 116 configured for voltage sensing may simultaneously also be configured for current injection, while a second electrode configured for voltage sensing may simultaneously ale be configured for current sensing.

Micro-relay circuits 302a-d execute switching using one or more micro-relay components. The micro-relay components advantageously switch between connecting and disconnecting current injection and/or current-sensing circuits to the electrodes with a minimum of parasitic impedances or capacitances (1-2 pF) added to the measuring circuit. By avoiding the addition of such parasitic impedances and capacitances, switching circuit 114 can switch between measuring subsets 206a-c quickly without sacrificing the accuracy of the collected electrical measurements. Micro-relay circuits 302a-d also provide the advantage of using electrical switches instead of slower mechanical rotary switches.

Figure 4:
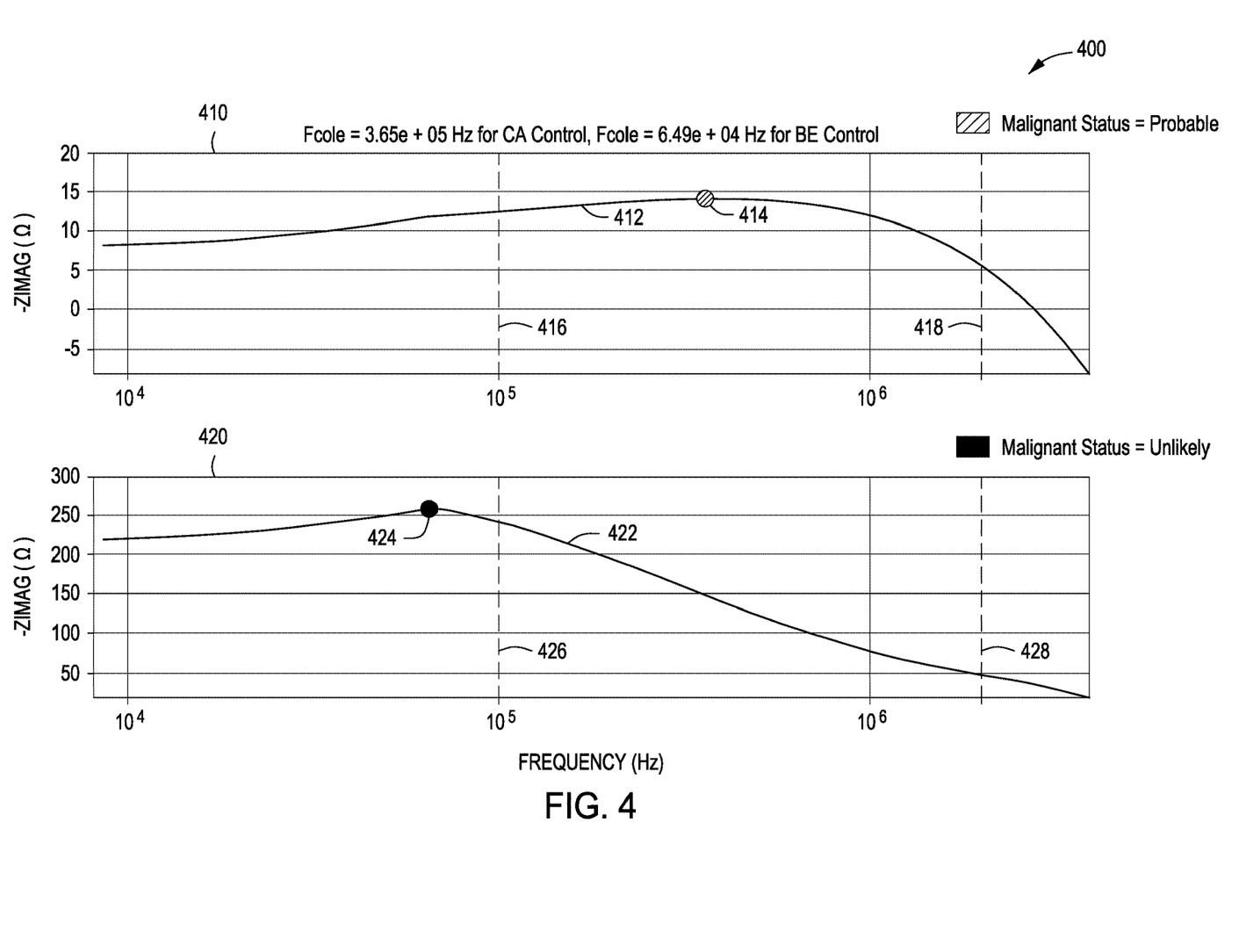
FIG. 4 illustrates computed Cole relaxation frequencies for multiple sections of excised tissue, according to various embodiments of the present invention.

In some embodiments, micro-relay circuits 302a-d may include one or more correction techniques to minimize crosstalk caused by one or more electrodes in electrode array 116 when a measuring subset 206a is performing an electrical measurement. For example, one or more electrodes of electrode array 116 may be connected to a Reed relay, such as a 1 pF capacitor (not shown) to limit crosstalk for electrodes in electrode array 116 that are not included in the measuring subset 206a. In some embodiments, micro-relay circuits 302a-d may match impedances of FIG. 4 illustrates computed Cole relaxation frequencies for multiple sections of excised tissue, according to various embodiments of the present invention. Graphs 400 illustrate impedance spectrums indicating calculated impedances for a range of operating frequencies based on voltages and currents measured by electrode array 116. Graph 410 illustrates impedance spectrum 412 for a section of an excised tissue sample that likely includes malignant cells. Graph 420 illustrates impedance spectrum 423 for a section of an excised tissue sample that likely does not include any malignant cells.

Graph 410 includes cancer-detecting threshold 416 and critical stage threshold 418. Impedance spectrum 412 includes a Cole relaxation frequency 414 corresponding to the peak of impedance spectrum 412. In some embodiments, analyzer 121 computes Cole relaxation frequency 414 by generating an impedance spectrum 412 and determining the frequency corresponding to the peak of the curve. In some embodiments, analyzer 121 may compare Cole relaxation frequency with cancer-detection threshold 416 and/or critical stage threshold 418.

For example, analyzer 121 can compare Cole relaxation frequency 414 to cancer-detection threshold 416. In some embodiments, cancer-detection threshold 416 can range from 100 kHz to 600 kHz. Analyzer 121 can determine that the section of the excised tissue sample likely contains malignant cells because Cole relaxation frequency 414 exceeds cancer-detection threshold 416. In contrast, analyzer 121 may determine compare Cole relaxation frequency 424 for impedance spectrum 422 to cancer-detection threshold 426. Analyzer 121 can determine that the section of the excised tissue sample likely does not contain malignant cells because Cole relaxation frequency 424 is less than cancer-detection threshold 426. In some instances, Cole relaxation frequency 414 for a tissue sample containing malignant cancer cells is approximately 1000 times larger than Cole relaxation frequency 424 for a tissue sample that does not contain any malignant cancer cells.

In some embodiments, analyzer 121 may compare Cole relaxation frequency 414 to a critical stage threshold 418. In some embodiments, critical stage threshold 428 can range from 1 MHz to 2 MHz. Analyzer 121 can determine that the section of the excised tissue sample does not contain cells likely approaching a critical stage indicating more dangerous concentrations of cancer cells because Cole relaxation frequency 414 is below critical stage threshold 418. Similarly, analyzer 121 may compare Cole relaxation frequency 424 to critical stage threshold 428. Analyzer 121 can determine that the section of the excised tissue sample likely does not contain cells likely approaching a critical stage indicating more dangerous concentrations of cancer cells because Cole relaxation frequency 424 is less than critical stage threshold 428. In some embodiments, analyzer 121 may compare Cole relaxation frequency 424 to multiple critical stage thresholds, where each critical stage threshold indicating a higher probability of cancer and/or a more dangerous diagnosis.

Figure 5:
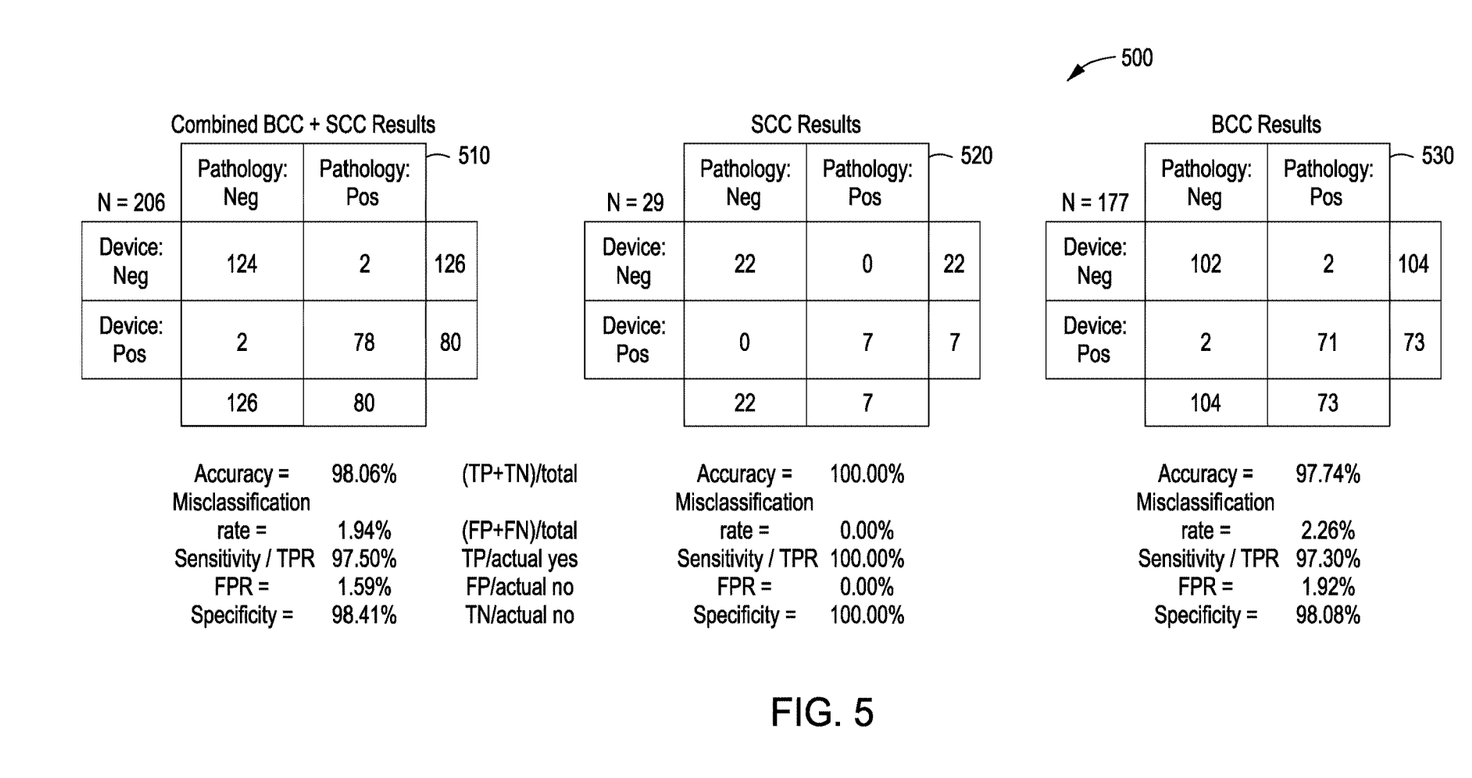
FIG. 5 illustrates tables showing the accuracies of cancer detection in a sample group of patients based on various computed Cole relaxation frequencies, according to various embodiments of the present invention.

FIG. 5 illustrates tables showing the accuracies of cancer detection in a sample group of patients based on various computed Cole relaxation frequencies, according to various embodiments of the present invention. Tables 500 show tabulated results of diagnosis for squamous cell carcinomas (SCCs) 520, basal cell carcinomas (BCCs) 530, and combined results 510 for a group of patients using tissue measurement system 100.

Table 530 shows that from a sample of 177 tests for basal cell carcinoma, tissue measurement system 100 accurately classified over 97 percent of the excised tissue samples. The accuracy of the tissue measurement system includes a high sensitivity rate, reflecting the rate at which tissue measurement system 100 correctly detected malignant cells in excised tissue that actually contained malignant cells. The accuracy of the tissue measurement system also includes a high specificity rate, reflecting the rate at which tissue measurement system 100 correctly detected no malignant cells in excised tissue that actually contained no malignant cells.

Table 520 shows that from a sample of 29 tests for squamous cell carcinoma, tissue measurement system 100 accurately classified each of the excised tissue samples. Table 510 shows that tissue measurement system 100 accurately detected the presence or absence of BCCs or SCCs in over 98 percent of excised tissue samples. Tissue measurement system 100 provides a technological improvement over prior devices in automatically detecting cancerous cells in an excised tissue sample quickly and with high accuracy.

Figure 6:
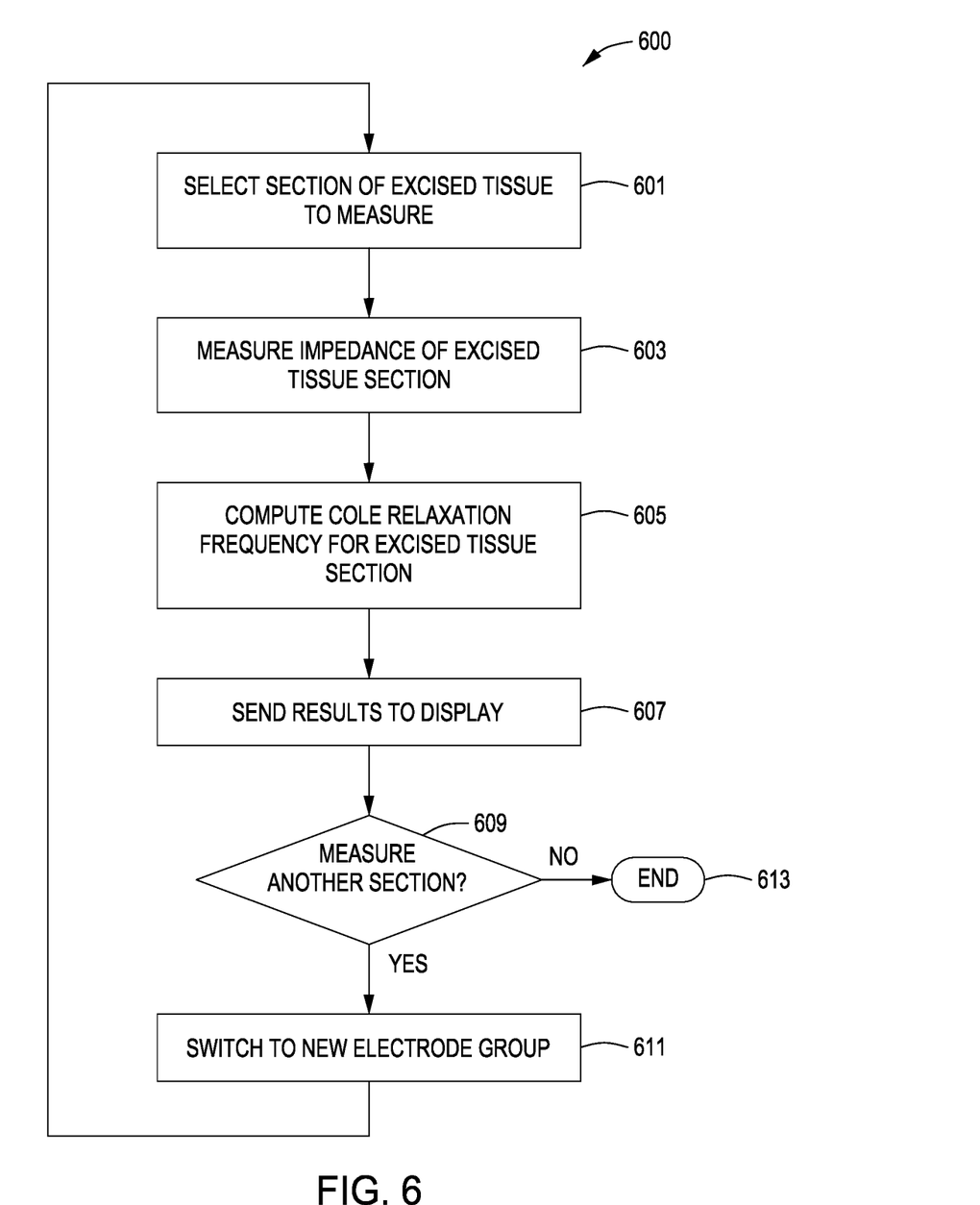
FIG. 6 is a flow diagram of method steps for automatically analyzing and assessing samples of excised tissue for cancer cells, according to various embodiments of the present invention.

FIG. 6 is a flow diagram of method steps for automatically analyzing and assessing samples of excised tissue for cancer cells, according to various embodiments of the present invention. Although the method steps described in conjunction with the systems of FIGS. 1-4, persons skilled in the art will understand that any system configured to perform the method steps, in any order, is within the scope of the invention.

As shown, a method 600 for automatically analyzing and assessing an excised tissue sample starts at step 601, where diagnosis module 112 of tissue measurement device 110 selects a section of the excised tissue sample to measure. Controller 123 included in diagnosis module 112 sends a control signal to switching circuit 114 to connect a measuring subset 206a of electrode array 116 that surrounds the selected section. In some embodiments, controller 123 selects the section of the excised tissue sample based on an instructions from a program loaded from memory 125. In some embodiments, controller 123 selects the section of the excised tissue sample based on a user input received via I/O units 130.

At step 603, tissue measurement device 110 measures at least one impedance of the section of the excised tissue sample. In some embodiments, controller 123 may cause switching circuit 114 to sweep through operating frequencies of a measurement circuit in order to measure voltages and currents for the section of the excised tissue sample. In some embodiments, diagnosis module 112 may store the measured voltage and current at each operating frequency in memory 125. In some embodiments, analyzer 121 in diagnosis module 112 may compute an impedance for a given operating frequency as a ratio of the measured voltage and the measured current.

At step 605, diagnosis module 112 of tissue measurement device 110 computes a Cole relaxation frequency 414, 424 for the section of the excised tissue sample. In some embodiments, analyzer 121 of diagnosis module 112 may compute a Cole relaxation frequency 414, 424 based on the one or more impedances computed for the section of the excised tissue sample. In some embodiments, analyzer 121 may calculate the Cole relaxation frequency 414, 422 based on impedance at a single operating frequency. In some embodiments, analyzer 121 may generate an impedance spectrum from a set of impedances computed at multiple operating frequencies. Analyzer 121 may then compute the Cole relaxation frequency 414, 424 by determining the peak of the impedance spectrum 412, 422 and determining the frequency at which the peak occurs.

At step 607, diagnosis module 112 of tissue measurement device 110 sends one or more of the computed results to display. In some embodiments, analyzer 121 may determine the presence or absence of cancerous cells based on the Cole relaxation frequency 414, 424. Analyzer 121 compares the Cole relaxation frequency 414, 424 of the section of the excised tissue sample to a cancer-detection threshold 416, 426 and generates an indication that the section contains cancerous cells when the Cole relaxation frequency 414, 424 exceeds the cancer-detection threshold 418, 428. In some embodiments, analyzer 121 may generate a mapping image that identifies the location of the cancerous cells, corresponding to the sections of the excised tissue sample that analyzer 121 determined contain cancerous cells. Analyzer 121 may send the cancer detection indicator and/or mapping image to display 120.

At step 609, diagnosis module 112 of tissue measurement device 110 determines whether to measure another section of the excised tissue sample. Controller 123 may determine to measure another section of the excised tissue sample when executing instructions to measure multiple sections of the excised tissue sample in a pre-defined sequence. For example, controller 123 may execute instructions to measure consecutive sections of the excised tissue sample using a single column of electrodes 202a-l in electrode array 116. When controller 123 determines to measure another section, diagnosis module 112 proceeds to step 611, otherwise, method 600 ends at step 613.

At step 613, diagnosis module 112 of tissue measurement device 110 selects a different measuring subset 206b of electrode array 116 to measure a different section of the excised tissue sample. In some embodiments, controller 123 causes switching circuit 114 to disconnect one or more electrodes from previous measuring subset 206a and connect electrodes in measuring subset 206b to a measuring circuit. After switching to the new measuring subset 206b, tissue measurement device 110 returns to step 601.

Figure 7:
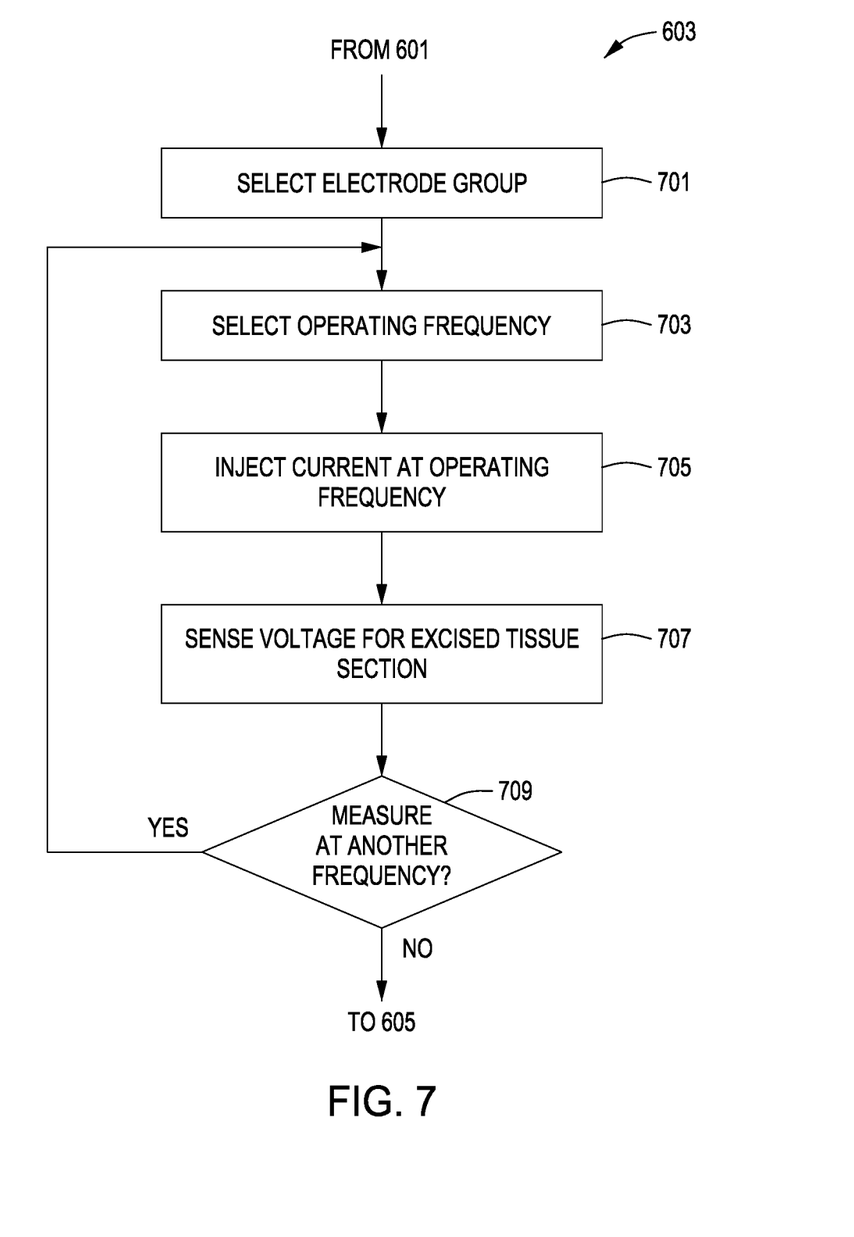
FIG. 7 is a flow diagram of method steps for detecting impedances for a section of excised tissue, according to various embodiments of the present invention.

FIG. 7 is a flow diagram of method steps for detecting impedances for a section of excised tissue, according to various embodiments of the present invention. Although the method steps described in conjunction with the systems of FIGS. 1-4, persons skilled in the art will understand that any system configured to perform the method steps, in any order, is within the scope of the invention.

Method 603 occurs between step 601 and step 605 of method 600. As shown, method 603 starts at step 701, where controller 123 of diagnosis module 112 selects a group of electrodes to measure the select section of the excised tissue sample. Controller 123 causes switching circuit 114 to connect measuring subset 206a to measuring circuit. In some embodiments, controller 123 causes switching circuit 114 to short to ground all remaining electrodes in electrode array 116.

At step 703, controller 123 selects an operating frequency for a measuring alternating current. In some embodiments, controller 123 sends a control signal to switching circuit 114 that includes a signal generator. Controller 123 causes the signal generator in switching circuit 114 to generate a measuring signal that has an alternating current, where the frequency of the alternating current is the operating frequency.

At step 705, switching circuit 114 injects the measuring signal at the operating frequency. In some embodiments, switching circuit 114 injects the measuring signal by connecting an electrode pair in measuring subset 206 to the signal generator to close a current path. In some embodiments, the current path may include a current-sensing circuit or a current-sensing device that measures the current of the measuring signal.

At step 707, switching circuit 114 senses a voltage for the section of the excised tissue sample. In some embodiments, switching circuit 114 connects one or more electrodes 202b-c to a voltage-sensing circuit or device. The one or more electrodes 202b-c are physically located in between the electrode pair forming the current path. The one or more electrodes 202b-c provide a high-impedance voltage-sensing circuit that does not introduce stray currents into the current path carrying the measuring signal. In some embodiments, the voltage-sensing circuit measures the voltage of the section of the excised tissue sample located in between the one or more electrodes 202b-c included in the voltage-sensing circuit.

At step 709, controller 123 in diagnosis module 112 determines whether to measure the electrical properties of the section of the excised tissue at another frequency. In some embodiments, controller 123 may change the operating frequency of the measuring signal as part of a frequency sweep to measure the same section of the excised tissue sample using multiple operating frequencies. In some embodiments, controller 123 may increase the operating frequency at a constant rate over a specified range of frequencies. For example, controller 123 may set an initial operating frequency of 1 kHz and increase the operating frequency by 50 kHz until reaching a final operating frequency of 1 MHz. When controller 123 determines that the measuring circuit is to perform measurements at another frequency, controller 123 returns to step 703, otherwise, controller 123 proceeds to step 605 of method 600.

In sum, the tissue measurement system disclosed herein enables cancerous cells to be detected automatically within a sample of excised tissue based on the measured impedances of sections of the excised tissue. A controller in the tissue measurement system uses a switching circuit to select a first subset of electrodes in an electrode array, where the first subset of electrodes transmits a current through a given section of the excised tissue. As the current is transmitted through the given section of excised tissue, an analyzer included in the tissue measurement system measures the electrical impedance of the given section of excised tissue. The analyzer then computes a Cole relaxation frequency for the given section of excised tissue based on the measured electrical impedance. The Cole relaxation frequency for the given section of excised tissue reflects the rate at which cell membranes discharge stored electrical charges. The analyzer compares the computed Cole relaxation frequency given for the section of excised tissue to a threshold. If the computed Cole relaxation frequency for the given section of excised tissues exceeds the threshold, then cancerous cells are considered to be present in the given section of excised tissue.

In some embodiments, the switching circuit includes a separate micro-relay connected to each of the electrodes in the electrode array in order to prevent the electrode array from introducing crosstalk signals, stray impedances, or other parasitic electrical charges into the measured impedances of the different sections of excised tissue. In some embodiments, the controller causes the switching circuit to select different subsets electrodes in of the electrode array to determine impedances for different sections of the excised tissue. Accordingly, the analyzer can determine the presence of cancerous cells for each section of the excised tissue based on the respective impedances measured for those sections. The analyzer also indicates each location of detected cancerous cells based on the locations of the different sections determined to include cancerous cells.

A major advantage of the disclosed techniques is that the tissue measurement system enables a user to quickly detect the presence and location of cancer cells in a tissue with a high degree of accuracy based on the computed Cole relaxation frequency. Detecting cancerous cells based on the Cole relaxation frequency enables a surgeon to maintain high accuracy when assessing excised tissue during MMS without requiring frozen section preparation and microscopic evaluation of each excised tissue layer, greatly reducing the procedural time of MMS. The reduction in time of MMS also greatly reduces the cost of performing MMS as a treatment for skin cancer.

Another advantage of the disclosed techniques is that the tissue measurement system includes micro-relay components that advantageously switch between connecting and disconnecting the electrodes to measure the electrical properties of the excised tissue sample without introducing parasitic impedances or capacitances. Avoiding the addition of parasitic impedances and capacitances enables the tissue measurement system switch connections to different electrodes quickly without sacrificing the accuracy of the collected electrical measurements.

1. In some embodiments, a method for detecting cancerous cells in a sample of excised tissue comprises measuring, by a first subset of electrodes included in an electrode array at a first operating frequency, a first impedance of a first section of the sample; computing a first Cole relaxation frequency for the first section of the sample based on the first impedance; and determining that the first section of the sample contains cancerous cells based on the first Cole relaxation frequency.

2. The method of clause 1, which further comprises measuring, by a second subset of electrodes included in the electrode array at the first operating frequency, a second impedance of a second section of the sample.

3. The method of clause 1 or 2, which further comprises computing a second Cole relaxation frequency for the second section of the sample based on the second impedance; determining that the second section of the tissue contains cancerous cells based on the second Cole relaxation frequency; and determining positions of cancerous cells in the sample based on a position of the first section within the sample and a position of the second section within the sample.

4. The method of any of clauses 1-3, which further comprises measuring, by a second subset of electrodes included in an electrode array at a first operating frequency, a second impedance of the first section of the sample; computing a second Cole relaxation frequency for the first section of the sample based on the second impedance; determining that the second section of the tissue contains cancerous cells based on the second Cole relaxation frequency; and determining positions of cancerous cells in the sample based on a position of the first section within the sample.

5. The method of any of clauses 1-4, wherein the first Cole relaxation frequency comprises an average rate of electrical discharge associated with a plurality of cell membranes included in the first section of the sample.

6. The method of any of clauses 1-5, where determining that the first section of the tissue contains cancerous cells comprises determining that the first Cole relaxation frequency exceeds a first threshold.

7. The method of any of clauses 1-6, where measuring the first impedance of the first section of the sample comprises injecting, at a first electrode included in the first subset of electrodes, a first alternating current at the first operating frequency; returning, at a second electrode included in the first subset of electrodes, the first alternating current; and measuring, at one or more electrodes located in between the first electrode and the second electrode, a voltage associated with the first section of the sample as the alternating current passes through the first section of the sample.

8. In some embodiments, an apparatus for detecting cancerous cells in a sample of excised tissue comprising a first subset of electrodes included in an electrode array configured to measure, at a first operating frequency, a first impedance of a first section of the sample; and an analyzer configured to determine a first Cole relaxation frequency for the first section of the sample based on the first impedance; and determine that the first section of the sample contains cancerous cells based on the first Cole relaxation frequency.

9. The apparatus of clause 8, where the first subset of electrodes comprises a first electrode; a second electrode parallel to the first electrode; and a third electrode parallel to the first and second electrode, wherein a first distance between the first electrode and second electrode is equal to a second distance between the second electrode and third electrode.

10. The apparatus of clause 8-9, where the first subset of the electrodes comprises a first electrode configured to inject a first alternating current at the first operating frequency; a second electrode configured to return the first alternating current; and at least one third electrode located in between the first electrode and the second electrode, wherein the at least one third electrode is configured to measure a voltage associated with the first section of the sample as the alternating current passes through the first section of the sample.

11. The apparatus of any of clauses 8-10, which further comprises a switching circuit connected to the electrode array, wherein the switching circuit is configured to electrically connect the first subset of electrodes and electrically disconnect all remaining electrodes in the electrode array when the first subset of electrodes measures the first impedance.

12. The apparatus of any of clauses 8-11, where the switching circuit includes a plurality of micro relays, wherein each micro relay in the plurality of micro relays is connected to a separate electrode in the electrode array.

13. The apparatus of any of clauses 8-12, which further comprises a second subset of electrodes included in the electrode array configured to measure, at the first operating frequency, a second impedance of a second section of the sample; and a controller configured to electrically connect, via the switching circuit, the first subset of electrodes when measuring the first impedance, and electrically connect, via the switching circuit, the second subset of electrodes when measuring the second impedance.

14. The apparatus of any of clauses 8-13, where a first electrical path length for the first subset of electrodes is equal to a second electrical path length for the second subset of electrodes.

15. The apparatus of any of clauses 8-14, where the first operating frequency is a frequency between 1 kHz and 25 MHz.

16. The apparatus of any of clauses 8-15, where at least one electrode in the electrode array comprises a platinum electrode.

17. The apparatus of any of clauses 8-16, where each electrode in the electrode array comprises a non-invasive electrode that is substantially flat when contacting the sample.

18. In some embodiments, a non-transitory computer-readable medium including instructions that, when executed by a processor, cause the processor to perform the steps of receiving, from a first subset of electrodes included in an electrode array measuring at a first operating frequency, a first impedance of a first section of a sample of excised tissue; computing a first Cole relaxation frequency for the first section of the sample based on the first impedance; and determining that the first section of the sample contains cancerous cells based on the first Cole relaxation frequency.

19. The non-transitory computer-readable medium of clause 18, where the instructions further cause the processor to perform the steps of receiving, from a second subset of electrodes included in the electrode array measuring at the first operating frequency, a second impedance of a second section of the sample; computing a second Cole relaxation frequency for the second section of the sample based on the second impedance; determining that the second section of the tissue contains cancerous cells based on the second Cole relaxation frequency; and determining positions of cancerous cells in the sample based on a position of the first section within the sample and a position of the second section within the sample.

20. The non-transitory computer-readable medium of claim 18, where the instructions further cause the processor to perform the step of measuring, by a second subset of electrodes included in an electrode array at a first operating frequency, a second impedance of the first section of the sample; computing a second Cole relaxation frequency for the first section of the sample based on the second impedance; determining that the second section of the tissue contains cancerous cells based on the second Cole relaxation frequency; and determining positions of cancerous cells in the sample based on a position of the first section within the sample.

Any and all combinations of the claim elements recited in any of the claims and/or any elements described in this application, in any fashion, fall within the contemplated scope of the present invention and protection.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments.

Aspects of the present embodiments may be embodied as a system, method or computer program product. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Aspects of the present disclosure are described above with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine. The instructions, when executed via the processor of the computer or other programmable data processing apparatus, enable the implementation of the functions/acts specified in the flowchart and/or block diagram block or blocks. Such processors may be, without limitation, general purpose processors, special-purpose processors, application-specific processors, or field-programmable gate arrays.

The flowchart and block diagrams in the Figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

While the preceding is directed to embodiments of the present disclosure, other and further embodiments of the disclosure may be devised without departing from the basic scope thereof, and the scope thereof is determined by the claims that follow.

What is claimed is:

1. A method for detecting cancerous cells in a sample of excised tissue, the method comprising:
    electrically connecting, by a switching circuit connected to an electrode array, a first subset of electrodes;
    measuring, by the first subset of electrodes at a first set of operating frequencies, a first set of electrical properties corresponding to a first section of the sample, wherein the switching circuit connects a second subset of electrodes included in the electrode array to a separate set of one or more contacts when the first subset of electrodes measures the first set of electrical properties;
    computing, from the first set of electrical properties, a first set of impedances;
    computing, from the first set of impedances, a first Cole relaxation frequency for the first section of the sample;
    comparing the first Cole relaxation frequency to a first threshold; and
    determining, when the first Cole relaxation frequency exceeds the first threshold, that the first section of the sample contains cancerous cells.

2. The method of claim 1, further comprising
    measuring, by a third subset of electrodes included in the electrode array at the first set of operating frequencies, a second set of electrical properties corresponding to a second section of the sample,
    wherein the switching circuit connects a fourth subset of electrodes included in the electrode array to the separate set of one or more contacts when the third set of electrodes measures the second set of electrical properties.

3. The method of claim 2, further comprising:
computing, from the second set of electrical properties, a second set of impedances;
computing, from the second set of impedances, a second Cole relaxation frequency for the second section of the sample;
comparing the second Cole relaxation frequency to the first threshold;
determining, when the second Cole relaxation frequency exceeds the first threshold, that the second section of the tissue contains cancerous cells; and
determining, based on a position of the first section within the sample and a position of the second section within the sample, one or more positions of cancerous cells in the sample.

4. The method of claim 1, further comprising:
measuring by a third subset of electrodes included in the electrode array at the first set of operating frequencies, a second set of electrical properties corresponding to the first section of the sample, wherein the switching circuit connects a fourth subset of electrodes included in the electrode array to the separate set of one or more contacts when the third subset of electrodes measures the second set of electrical properties;
computing, from the second set of electrical properties, a second set of impedances;
computing, from the second set of impedances, a second Cole relaxation frequency for the first section of the sample;
determining, when the second Cole relaxation frequency exceeds the first threshold, that the first section of the tissue contains cancerous cells; and
determining, based on a position of the first section within the sample, one or more positions of cancerous cells in the sample.

5. The method of claim 1, wherein the first Cole relaxation frequency comprises an average rate of electrical discharge associated with a plurality of cell membranes included in the first section of the sample.

6. The method of claim 1, wherein measuring the first set of electrical properties corresponding to the first section of the sample comprises:
injecting, at a first electrode included in the first subset of electrodes, a first alternating current at a first operating frequency included in the first set of operating frequencies;
returning, at a second electrode included in the first subset of electrodes, the first alternating current; and
measuring, at one or more electrodes located in between the first electrode and the second electrode, a voltage associated with the first section of the sample as the alternating current passes through the first section of the sample.

7. An apparatus for detecting cancerous cells in a sample of excised tissue, the apparatus comprising:
an electrode array comprising:
a first subset of electrodes that measures, at a first set of operating frequencies, a first set of electrical properties corresponding to of a first section of the sample; and
a second subset of electrodes that are connected to a separate set of one or more contacts when the first subset of electrodes measures the first set of electrical properties; and a switching circuit connected to the electrode array that:
electrically connects the first subset of electrodes; and
connects the second subset of electrodes to the separate set of one or more contacts;
an analyzer that:
computes, from the first set of electrical properties, a first set of impedances;
computes, from the first set of impedances, a first Cole relaxation frequency for the first section of the sample;
compares the first Cole relaxation frequency to a first threshold; and
determines, when the first Cole relaxation frequency exceeds the first threshold, that the first section of the sample contains cancerous cells.

8. The apparatus of claim 7, wherein the first subset of electrodes comprises:
a first electrode;
a second electrode parallel to the first electrode; and
a third electrode parallel to the first and second electrode, wherein a first distance between the first electrode and second electrode is equal to a second distance between the second electrode and third electrode.

9. The apparatus of claim 7, wherein the first subset of the electrodes comprises:
a first electrode configured to inject a first alternating current at a first operating frequency included in the first set of operating frequencies;
a second electrode configured to return the first alternating current; and
at least one third electrode located in between the first electrode and the second electrode,
wherein the at least one third electrode is configured to measure a voltage associated with the first section of the sample as the alternating current passes through the first section of the sample.

10. The apparatus of claim 7, wherein:
the switching circuit includes a plurality of micro relays, and
each micro relay included in the plurality of micro relays is connected to a separate electrode in the electrode array.

11. The apparatus of claim 7, wherein:
the electrode array includes a third subset of electrodes included in the electrode array that measures, at the set of first operating frequencies, a second set of electrical properties corresponding to a second section of the sample; and
further comprising a controller that:
electrically connects, via the switching circuit, the first subset of electrodes when measuring the first set of electrical properties, and
electrically connects, via the switching circuit, the third subset of electrodes when measuring the second set of electrical properties.

12. The apparatus of claim 11, wherein a first electrical path length for the first subset of electrodes is equal to a second electrical path length for the third subset of electrodes.

13. The apparatus of claim 7, wherein the first set of operating frequencies includes a frequency between 1 kHz and 25 MHz.

14. The apparatus of claim 7, wherein at least one electrode in the electrode array comprises a platinum electrode.

15. The apparatus of claim 7, wherein each electrode in the electrode array comprises a non-invasive electrode that is substantially flat when contacting the sample.

16. One or more non-transitory computer-readable media including instructions that, when executed by one or more processors, cause the one or more processors to perform the steps of:
receiving, from a first subset of electrodes included in an electrode array measuring at a first set of operating frequencies, a first set of electrical properties corresponding to a first section of a sample of excised tissue, wherein:
a switching circuit, connected to the electrode array, electrically connects the first subset of electrodes; and
the switching circuit connects a second subset of electrodes included in the electrode array separate set of one or more contacts when the first subset of electrodes measures the first set of electrical properties;
computing, from the first set of electrical properties, a first set of impedances;
computing, from the first set of impedances, a first Cole relaxation frequency for the first section of the sample; and
comparing the first Cole relaxation frequency to a first threshold; and
determining, when the first Cole relaxation frequency exceeds the first threshold, that the first section of the sample contains cancerous cells.

17. The one or more non-transitory computer-readable media of claim 16, further including instructions that, when executed by the one or more processors, cause the one or more processors to perform the steps of:
receiving, from a third subset of electrodes included in the electrode array measuring at the first set of operating frequencies, a second set of electrical properties corresponding to a second section of the sample, wherein:
the switching circuit electrically connects the third subset of electrodes; and
the switching circuit connects a fourth subset of electrodes included in the electrode array to the separate set of one or more contacts when the third subset of electrodes measures the second set of electrical properties;
computing, from the second set of electrical properties, a second set of impedances;
computing, from the second set of impedances, a second Cole relaxation frequency for the second section of the sample;
comparing the second Cole relaxation frequency to the first threshold;
determining, when the second Cole relaxation frequency exceeds the first threshold, that the second section of the tissue contains cancerous cells; and
determining, based on a position of the first section within the sample and a position of the second section within the sample, one or more positions of cancerous cells in the sample.

18. The one or more non-transitory computer-readable media of claim 16, further including instructions that, when executed by the one or more processors, cause the one or more processors to perform the step of:
receiving, from a third subset of electrodes included in the electrode array measuring at the first set of operating frequencies, a second set of electrical properties corresponding to a second section of the sample, wherein:
the switching circuit electrically connects the third subset of electrodes; and
the switching circuit connects a fourth subset of electrodes included in the electrode array to the separate set of one or more contacts when the third subset of electrodes measures the second set of electrical properties;
computing, from the second set of electrical properties, a second set of impedances;
computing, from the second set of impedances, a second Cole relaxation frequency for the first section of the sample;
comparing the second Cole relaxation frequency to the first threshold;
determining, when the second Cole relaxation frequency exceeds the first threshold, that the first section of the tissue contains cancerous cells based on the second Cole relaxation frequency; and
determining, based on a position of the first section within the sample, one or more positions of cancerous cells in the sample.

* * * * *

UNITED STATES PATENT AND TRADEMARK OFFICE
CERTIFICATE OF CORRECTION

PATENT NO. : 10,758,151 B2
APPLICATION NO. : 15/870804
DATED : September 1, 2020
INVENTOR(S) : William David Gregory et al.

Page 1 of 1

It is certified that error appears in the above-identified patent and that said Letters Patent is hereby corrected as shown below:

In the Claims

Column 19, Claim 16, Line 17, insert --to a-- after array.

Signed and Sealed this
Thirtieth Day of March, 2021

Drew Hirshfeld
*Performing the Functions and Duties of the*
*Under Secretary of Commerce for Intellectual Property and*
*Director of the United States Patent and Trademark Office*